United States Patent [19]
Haskin

[11] Patent Number: 5,724,101
[45] Date of Patent: *Mar. 3, 1998

[54] SYSTEM FOR CONVERSION OF NON STANDARD VIDEO SIGNALS TO STANDARD FORMATS FOR TRANSMISSION AND PRESENTATION

[75] Inventor: Marvin E. Haskin, Philadelphia, Pa.

[73] Assignee: Prevail, Inc., Bryn Mawr, Pa.

[*] Notice: The portion of the term of this patent subsequent to Aug. 16, 2005, has been disclaimed.

[21] Appl. No.: 652,185

[22] Filed: Feb. 7, 1991

Related U.S. Application Data

[63] Continuation of Ser. No. 200,543, May 31, 1988, which is a continuation of Ser. No. 84,333, Aug. 11, 1987, which is a continuation-in-part of Ser. No. 36,264, Apr. 9, 1987.

[51] Int. Cl.$^6$ .............................. H04N 7/01; H04N 11/20
[52] U.S. Cl. .................. 348/441; 348/443; 348/445
[58] Field of Search ........................ 364/413.13, 413.22; 358/41, 140, 112; 348/441, 446, 445, 458, 459, 443

[56] References Cited

U.S. PATENT DOCUMENTS

| | | | |
|---|---|---|---|
| 4,213,147 | 7/1980 | von Buenay | 358/112 |
| 4,500,908 | 2/1985 | Mandeberg | 348/453 |
| 4,630,098 | 12/1986 | Fling | 348/449 |
| 4,658,293 | 4/1987 | Arai et al. | 348/448 |
| 4,670,783 | 6/1987 | Nadan | 358/141 |
| 4,694,336 | 9/1987 | Keesen et al. | 358/141 |
| 4,743,970 | 5/1988 | Barnett et al. | 348/717 |
| 4,764,870 | 8/1988 | Haskin | 364/413.13 |
| 4,777,486 | 10/1988 | Abraham et al. | 348/189 |
| 4,802,008 | 1/1989 | Walling | 348/13 |
| 4,872,054 | 10/1989 | Gray et al. | 348/441 |
| 5,005,126 | 4/1991 | Haskin | 364/413.13 |

FOREIGN PATENT DOCUMENTS 0212784  3/1987  European Pat. Off.

Primary Examiner—Gail O. Hayes
Assistant Examiner—Stephen R. Tkacs
Attorney, Agent, or Firm—Roberts & Brownell, LLC

[57] ABSTRACT

A system for conversion of non-standard video signals to standard video signals for transmission and presentation picks off an internal analog video signals from imaging diagnostic equipment (such as a CAT scanner or MRI equipment), converts it to analog video signal of different, preferably standard format, prints it or stores it, and when desire transmits the reformatted image information to the physician's terminal. Preferably the storage and transmission is in binary digitized form. At a receiving station, the received signal is stored, decoded and applied in appropriate analog vide form to an associated CRT display for reproduction of the diagnostic images. The equipments at both the control site of the diagnostic station and at the remote terminals may constitute PC's (personal computers) plus an additional video monitor. Preferably the converter equipment at the diagnostic site includes a monolithic signal processing chip which senses the format of the pick-off analog video and converts it to any desired output format.

10 Claims, 5 Drawing Sheets

SYSTEM FOR CONVERSION OF NON STANDARD VIDEO SIGNALS TO STANDARD FORMATS FOR TRANSMISSION AND PRESENTATION

REFERENCE TO OTHER APPLICATIONS

This is a continuation of application Ser. No. 07/200,543, filed May 31, 1988, which is a continuation of Ser. No. 084,333, filed Aug. 11, 1987, which is a continuation-in-part of Ser. No. 036,264, filed Apr. 9, 1987.

FIELD OF THE INVENTION

This invention relates to systems for presenting to a remote viewer images corresponding to diagnostic image information, and particularly to such systems for doing so by means of rapidly acting computerized digital telecommunications apparatus.

BACKGROUND OF THE INVENTION

There are many situations wherein it is desired to produce diagnostic image information with respect to a subject by means of any of a variety of electronic apparatuses, and for then making the results of these diagnostic tests promptly available to a person who is not present at the diagnosis site. This is especially true in the medical diagnosis of patients; prompt communication of diagnostic test results to a remote physician is not only often important for the physical well-being of the patient, but also shortens the stay of the patient in the hospital. This results in substantial economies of cost to the hospital, especially in view of the present economic system under which hospitals now typically operate, including for example the DRG and pre-admission certification systems.

In the past, one form of apparatus for providing such diagnostic image information has typically produced a photographic film record which is analyzed at a diagnostic station by an expert who prepares a diagnostic report, typically in written form, after which the film record and report are manually stored. The physician concerned may then go to the diagnostic station, have the films and reports retrieved and collated, and review them while there or, in some cases the materials may be mailed or otherwise delivered to him; both of these procedures are obviously very time-consuming. The report may instead be transmitted orally to the remote physician by telephone, in which case he does not have the benefit of viewing the visual diagnostic images himself, and a human operator is necessary to relay the report orally. In each of the above cases, which rely upon a written diagnosis and a photographic film, the basic analog information storage structures must be kept in files manually maintained for this purpose, for slow manual retrieval and collation when desired.

It would also be possible to provide an optical scanner or video camera at the diagnostic center, where the film record and typewritten commentary could be optically scanned or televised and the digitized results transmitted in binary digital form over telephone lines to a suitable computer and display screen at the physician's location. Such an arrangement would still require manual retrieval, collation and presentation of the film and written commentary to the optical scanning device or television camera, and is therefore again relatively slow and expensive; in addition, the use of a film record and subsequent televising or optical scanning of it generally results in substantial degradation of the quality of the diagnostic image transmitted to the remote physician.

At present, sophisticated diagnostic imaging techniques not only can provide a film record of the diagnostic image as described above, but can also produce and store a digitized reproduction of the film, so that the digitized image may be displayed at will, at the patient-testing site or remotely. As mentioned above, this approach is time-consuming and inherently inserts electrical noise into the resultant image, thus subjecting it to analog distortions.

It is also possible to derive from the digital storage files of the manufacturer's equipment a digitized version of the diagnostic image and transmit it to a remote station where it may be decoded by a D/A converter and the decoded information supplied to a cathode-ray tube display. Such a procedure has been found to be uneconomical, awkward and inaccurate for many applications. The manufacturers of such diagnostic equipment typically change the format of their respective digitized image files at will, which typically renders any previously-installed decoding system inoperative; a substantial and expensive effort is then required to analyze the new storage format, and to devise and install a new decoding system. Furthermore, the manufacturer's diagnostic equipment typically performs additional processing of the stored image-representing data after it is accessed and before it is displayed, so that transmitting the unprocessed stored digital data to the remote viewing site often results in a remote reproduced image substantially different from the image derived and displayed by the manufacturer's equipment at the subject-testing site.

It is therefore an object of this invention to provide a new and useful system and method for transmitting to a remote site diagnostic image information generated by an imaging modality at a subject-testing site.

Another object is to provide such a system and method which are capable of providing diagnostic image information to a physician at a remote site accurately and promptly, by means of apparatus which is easy to use yet inexpensive to construct, install, operate and maintain.

A further object is to provide such a system and method which remain operative despite changes in the data storage format in the imaging modality.

It is a further objective of the present invention to provide a means to convert from one analog format to another to allow printing at a given location where diagnostic imaging is taking place.

Still another object is to provide such a system and method which are capable of accessing image information from any of a plurality of different types of modalities in different formats, and for supplying such image information electronically to one or more remote display stations in a selected appropriate format.

SUMMARY OF THE INVENTION

These and other objects and features of the invention are achieved by the provision of a novel system and method which recognize and take advantage of the fact that the original equipment manufacturer's apparatus itself typically produces some form of analog video signal representating the diagnostic image information, in a format convenient for the manufacturer's purposes, and that the format of this signal is not often changed by the manufacturer, although it differs among different equipments and manufacturers. Such signal is typically used in real time to produce a local image of the diagnostic information, as an immediate aid to the diagnostician or his assistant in setting up the test and in monitoring its successful progress. Because this portion of the apparatus is typically embodied in hardware devices and circuitry, and hence is rather difficult and expensive to replace or modify substantially, original equipment manufacturers are loath to make frequent changes in it.

In accordance with the invention, the typical analog video signal produced in the original equipment manufacturer's diagnostic image-forming apparatus is picked off and converted to an analog video signal of a selected different, preferably standard, format for subsequent transmission to a remote terminal. Some typical examples of formats envisioned by the present invention are the Enhanced Graphics Adapter ("EGA") and Video Graphics Adapter ("VGA") standards commonly used with IBM standard personal computers and compatibles. This picked-off signal is preferably digitized and stored in its converted format, until it is desired to send the image information to the remote computer station for display. At such times, the stored digital data are accessed and transmitted to a remote station or terminal for decoding into the selected analog video format, for display.

Preferably but not necessarily, the signal sent to the remote terminal is in the NTSC format and transmission to the remote site is by a binary coded version of the NTSC signal sent over telephone lines of quality only sufficient to transmit the NTSC signal with good fidelity. The remote station preferably comprises a personal computer with a modem, disk drive, D/A converter, and separate cathode-ray tube monitor. With such an arrangement the desired transfer of diagnostic image information to the remote station is accomplished promptly, rapidly, accurately, with low cost of equipment and small expense for line-rental charges, and without need for frequent modification or replacement of equipment.

In a preferred embodiment the signal processing equipment at the central station includes a monolithic chip which enables the sensing of the format of the analog video signal and provides appropriate format conversion without requiring a special dedicated converter for each type of imaging equipment and preferably the programming is such as to permit selection of any of a variety of output formats.

BRIEF DESCRIPTION OF FIGURES

These and other objects and features of the invention will be more readily understood from a consideration of the following detailed description, taken with the accompanying drawings, in which.

DETAILED DESCRIPTION OF SPECIFIC EMBODIMENTS

Figure 1:
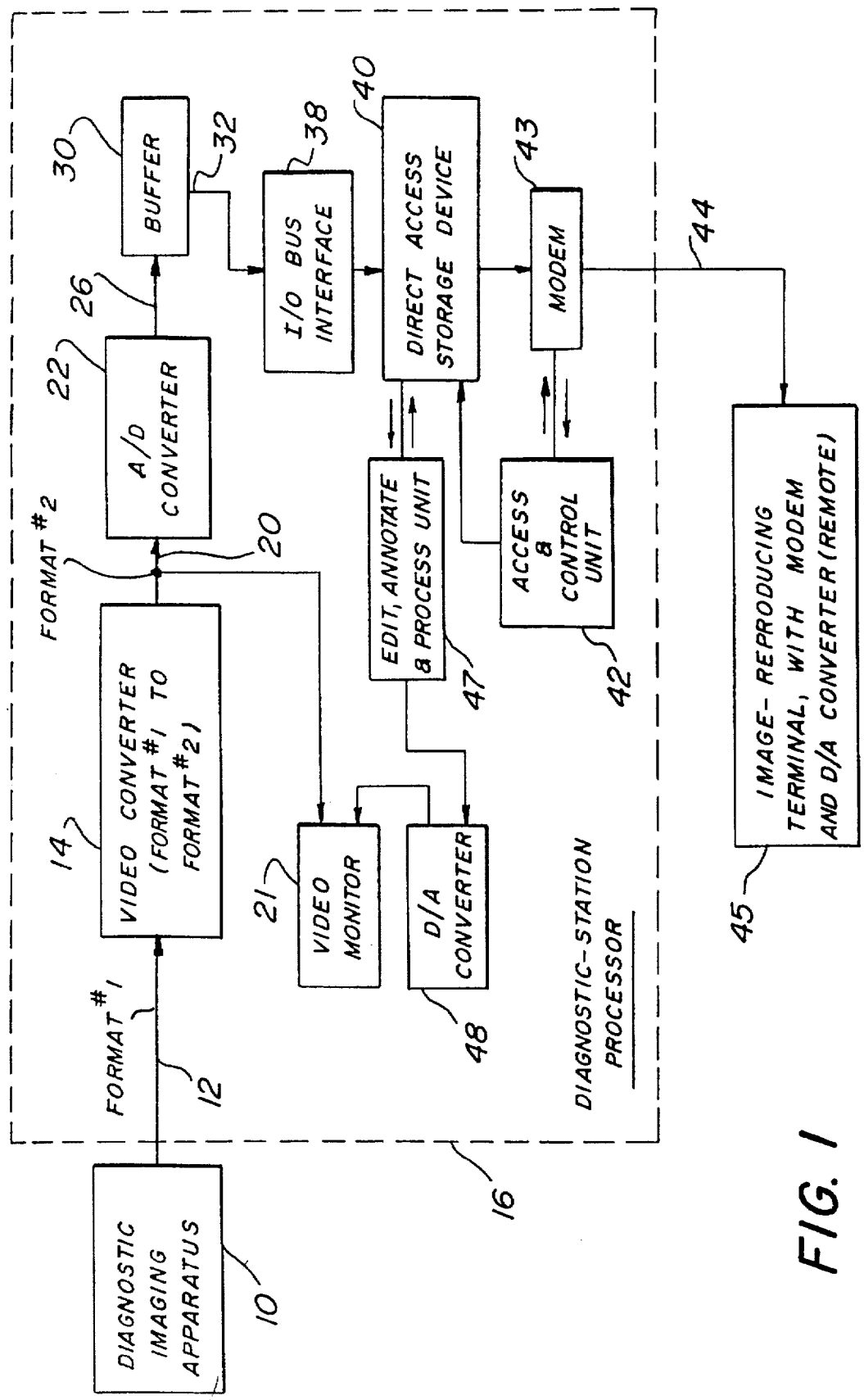
FIG. 1 is a broad block diagram illustrating a general system according to this invention.

Turning now to the specific embodiments of the invention illustrated in the drawings by way of example only, in FIG. 1 a diagnostic imaging apparatus 10 is shown which may be a standard original equipment manufacturer's apparatus, such as a computerized axial tomography unit (CAT scanner), a digital substraction angiography unit (DSA equipment), an ultrasonography apparatus (US), a magnetic resonance imager (MRI), or other medical or non-medical diagnostic imaging apparatus. It is assumed that it is of a usual present-day type which includes within it an internal line carrying an analog video signal of a first format representative of the diagnostic image. This signal may be in a non-standard format, for example with respect to its horizontal and/or vertical scanning frequencies and/or number of horizontal line scans per raster field. According to the present invention, a signal line 12 is tapped into the internal line carrying the latter analog video signal, and serves to deliver that signal to the video converter 14 in the diagnostic station processor 16, which converts this original video analog signal to a corresponding video analog signal in a second and different format, in this example a standard format.

More particularly, the video converter 14 changes the analog video signal on line 12 to a standard format which, when applied to a receiver-display device for receiving and displaying analog video signals of that standard format, will produce on the display device an image substantially the same as the image represented by the analog video signal on line 12. Preferred for this purpose, but not a limiting factor of the present invention, is the NTSC (National Television Systems Committee) standard format, or one compatible therewith. Other "standard" formats such as the EGA and VGA standard formats are also considered well within the capabilities of the present invention. The manner in which this conversion may be effected will be described more fully hereinafter with particular reference to FIGS. 3 and 4.

While for some purposes (e.g. for local distribution of the image) the converted video analog signal itself may be transmitted over an rf video transmission line, printed on a video printer in color or black-and-white preferably the standardized analog video signal on output line 20 of the video converter 14 before it is transmitted in digitized form. More particularly, and as shown in FIG. 1, it is applied both to a video monitor 21 on which it may be viewed and to an analog-to-digital converter 22 which digitizes the applied signal to form a corresponding digital bit stream on its output line 26. Line 26 supplies the bit stream to buffer 30 for temporary storage. The output of the buffer on line 32 supplies the buffered digital information to I/O Bus Interface 38 and thence to the Direct Access Storage Device 40 (DASD), which may be a disk-drive or other mass storage unit.

When it is desired that the stored image information in DASD 40 be transmitted for remote image-reproduction, an access and control unit 42 accesses the stored information and supplies it to modem 43 for transmission over link 44 to a remote image-reproducing terminal 45, which in this example includes a modem and a digital-to-analog converter for reducing the signal to its standard video analog form for application to the image-reproducing device, such as a cathode-ray tube, for visual reproduction of the diagnostic information. The link 44 may be a cable, telephone line, radio link or any other convenient transmission mechanism, although at present telephone lines are preferred.

To permit editing, annotating and other processing of the image represented by the data stored in storage device 40, an edit, annotate and process unit 47 may be connected to device 40, and selected contents of device 40 may be accessed and passed through a digital-to-analog converter 48 to video monitor 21 when so desired, so that the operator performing the editing, annotating and processing may see on monitor 21 the results of his efforts. This processing preferably includes 2:1 data compression, which results in a 4:1 reduction in digital data requirements, so as to permit a data transmission rate and storage requirements (both disk and D/A converter) which are one-fourth what would be the case without such compression.

Accordingly the diagnostic information derived by the diagnostic apparatus 10 is transmitted to the image-reproducing terminal 45 by picking-off the internal analog video from the imaging apparatus, converting it to a selected different standard format, temporarily storing it in a buffer, writing it into a disk drive and, when remote display is desired, accessing desired stored image information in the disk drive and transmitting it to the remote image-reproducing terminal in the binary-coded digital form of standard format, where it is decoded and applied to the remote video monitor in the desired analog format. Where the image information is diagnostic information as to a patient, a physician at the site of the remote image-reproducing terminal is thereby provided with the image information promptly, rapidly and inexpensively, as desired.

Figure 2:
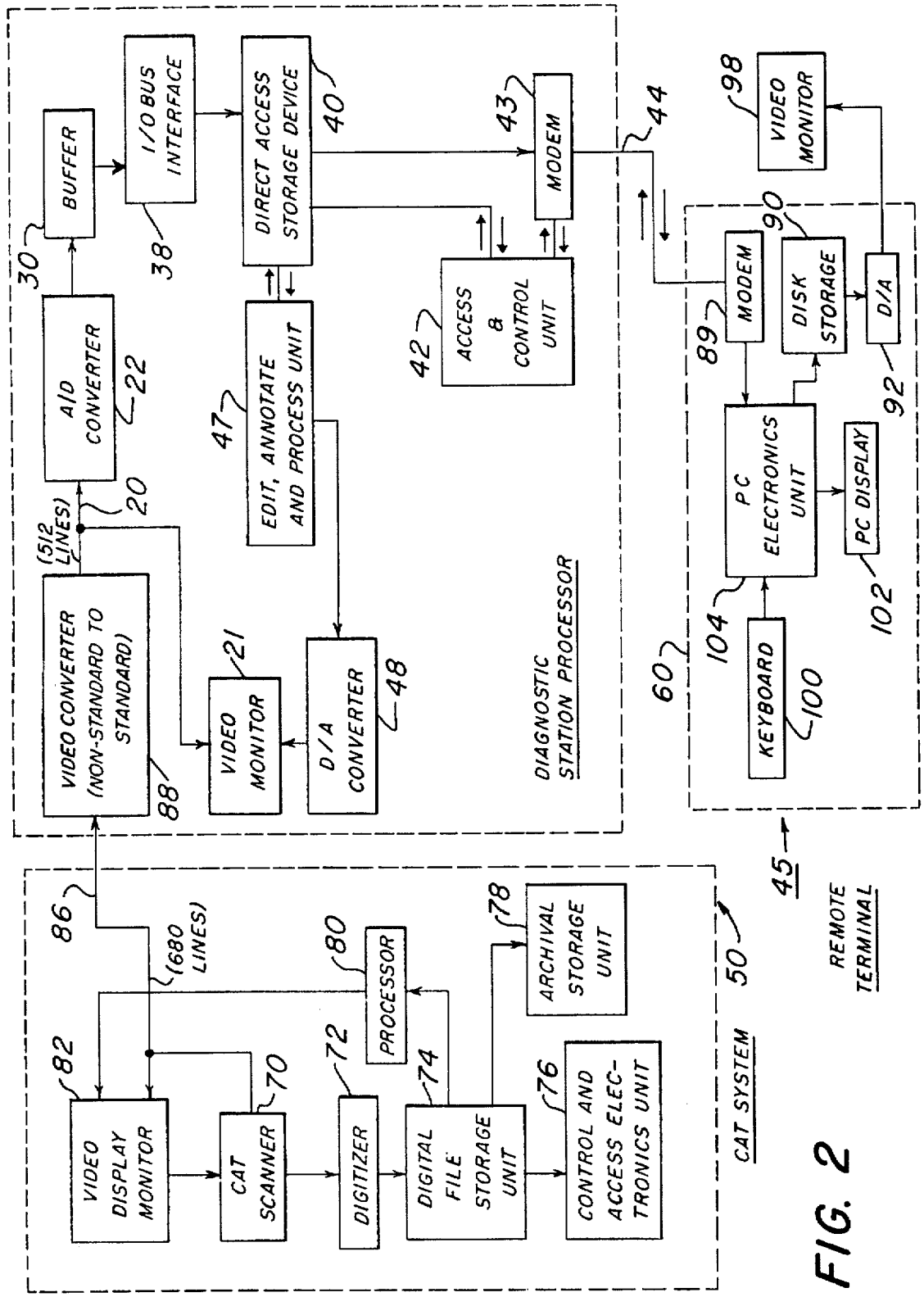
FIG. 2 is a more detailed block diagram of a system according to the invention as applied to a specific type of CAT scanner.
Figure 3:
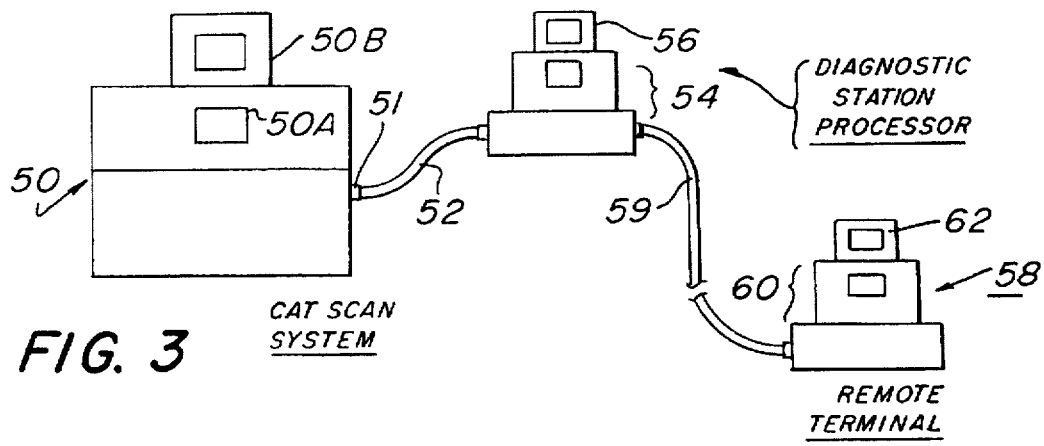
FIG. 3 is a schematic front elevational view of a preferred physical arrangement of the system of FIG. 2.

FIG. 2 illustrates an application of the invention to a CAT system 50 of the general type exemplified by the General Electric Model 8800 CAT system. Corresponding numerals in FIGS. 1 and 2 represent corresponding parts. FIG. 3 shows schematically the physical parts of the system of FIG. 2, comprising a CAT scan system 50 including its own main CRT display 50A and an auxiliary monochrome CRT display 50B for displaying the image-representing signal produced by the CAT scan equipment. A jack 51 on the CAT scan equipment supplies an rf analog video signal to coaxial line 52 in a non-standard format. Here it is assumed by way of example that the non-standard format has 680 horizontal scanning lines per frame, as is the case for the General Electric Model 8800 CAT scan unit. Near the CAT scan system is a diagnostic station processor, comprising in this example an IBM AT personal computer 54 or equivalent clone, including certain special internal circuit boards for performing special functions of this invention, plus a separate video monitor 56.

Remote from the diagnostic station processor is a remote terminal 58, in this example for use by a physician at his office or home, connected to the station processor by a telephone line 59 comprising two pairs of wires, so that the remote terminal and the diagnostic station processor can communicate with each other and so that the diagnostic station processor can send images generated by the CAT scanner to the physician's remote terminal; the physician can also communicate with the diagnostic station processor, for example with regard to what images he wishes to receive. The remote terminal in this example comprises an IBM XT PC clone computer 60, plus a separate video monitor 62 for viewing the images transmitted to it.

As shown in FIG. 2, the CAT system 50 may be functionally represented as comprising the CAT scanner 70 which actually irradiates the patient and derives an rf analog video signal of non-standard format, in this example having 680 horizontal line-scans per raster frame, interlaced 2:1. The latter image-representing signal is supplied to a digitizer 72, and the resultant digitized signal is supplied to a digital file storage unit 74. The storage unit 74 is controlled and accessed by electronics unit 76, to provide image information to archival storage unit 78 for long-term storage of the image information. The digital file storage unit is also controlled to deliver image information through a processor 80 to video display monitor 82.

The non-standard rf analog video signal generated by CAT scanner 70 may also be supplied directly, still in analog form, to video display monitor 82 to monitor the set-up and progress of the CAT scanning procedure. It is this non-standard rf analog video at 680 lines per frame which is picked off by coaxial television cable 86 and supplied to the diagnostic station processor.

The diagnostic station processor of FIG. 2 employs an image-grabbing video converter 88 supplied with the analog video on line 86, which converts the signal to a 525-line raster as described more fully hereinafter with particular reference to FIG. 3. The converted signal is again shown as passing through an A/D converter 22, a buffer 30 and an I/O bias interface 38 to be written in digitized form in the direct access storage device 40. At this point the edit, annotate and process unit 47 may be activated to select those images and parts of images to be retained for transmittal to the remote physician, to add annotations and pointers to the image, for example, and to perform other desired image-enhancing operations on the image data, after which they may be re-stored in device 40. The effect of these operations may be viewed by passing the processed signals through the D/A converter 48 to the video monitor 21 for viewing. When desired, the access and control unit 42 causes the binary coded NTSC signal in storage device to pass through modem 43 to telephone lines 44 and thence through modem 89 to the disk storage unit 90 of the remote terminal PC 60, from which it is transferred through the D/A converter board 92 in PC 60 to the external video monitor 98 for conversion to analog and display of the image. A conventional keyboard 100, PC display device 102 and PC electronics unit 104, with appropriate circuit boards to perform any desired special function, are also provided.

In operation of the system of FIG. 2, the CAT scanner is operated to produce the desired series of electronic diagnostic images, which are digitized and stored in its file storage unit 74, and permanently stored in archival storage unit 78. When accessed by electronics unit 76, storage unit 74 will pass the stored digital signals through processor 80 to video display monitor 82. The CAT scanner also supplies rf analog video versions of the 680-line CAT scan images over line 86 to video converter 14, where they are "frame grabbed" and converted to a 525 line raster for digitizing in A/D converter 22. The resultant binary digital data are temporarily stored in a 512 by×512 by 8 matrix in buffer 30, and then fed out through I/O interface 38 to storage device 40, where they constitute a stored data file for the particular image in question. As described previously, the file can be edited, annotated and otherwise processed as desired, including data compression as described above. When the physician at the remote PC terminal 45 wishes to view this image, he types-in appropriate identifying data and commands to access the data file for the selected images, which is then transferred out of storage device 40 through modem 43 and telephone lines 44 to the physician's remote PC terminal 60, wherein it is stored, passed through a D/A converter 92 to convert it to standard analog, and displayed on monitor 98. Various additional functions and features may also be provided, which are not necessarily part of the present invention.

Figure 4:
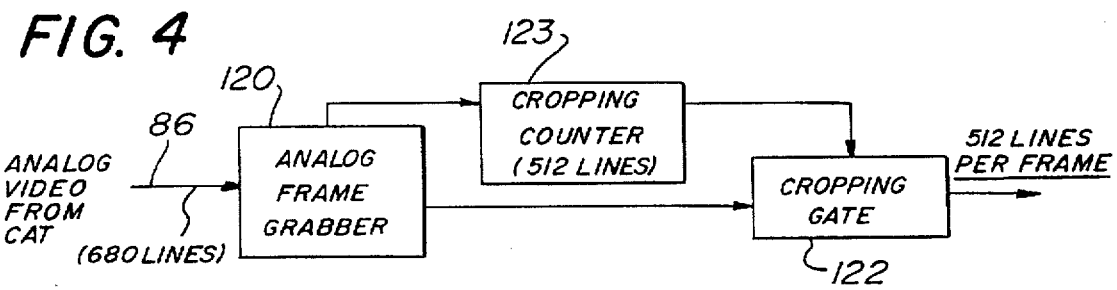
FIG. 4 is a block diagram showing an electrical arrangement of a video-conversion board suitable for converting the analog video signal from the CAT scanner of FIG. 2 to a standard rf NTSC analog video signal.

Referring now to FIG. 4, there is shown one way of converting the 680-line CAT scan analog video into 525-line video. The analog frame grabber 120 seizes and stores the signal corresponding to one complete CAT image supplied to it over line 86 from the CAT scan unit 50. The last 168 lines of the frame are "cropped", or removed, for example by passing the frame signal through a cropping gate 122 which is controlled by a cropping counter 123 to permit only the first 525 lines to pass; this is permissible because the last 168 lines at the bottom of the CAT scanner image contain no useful information. In this way the raster is limited to the 525 information-containing lines.

Figure 5:
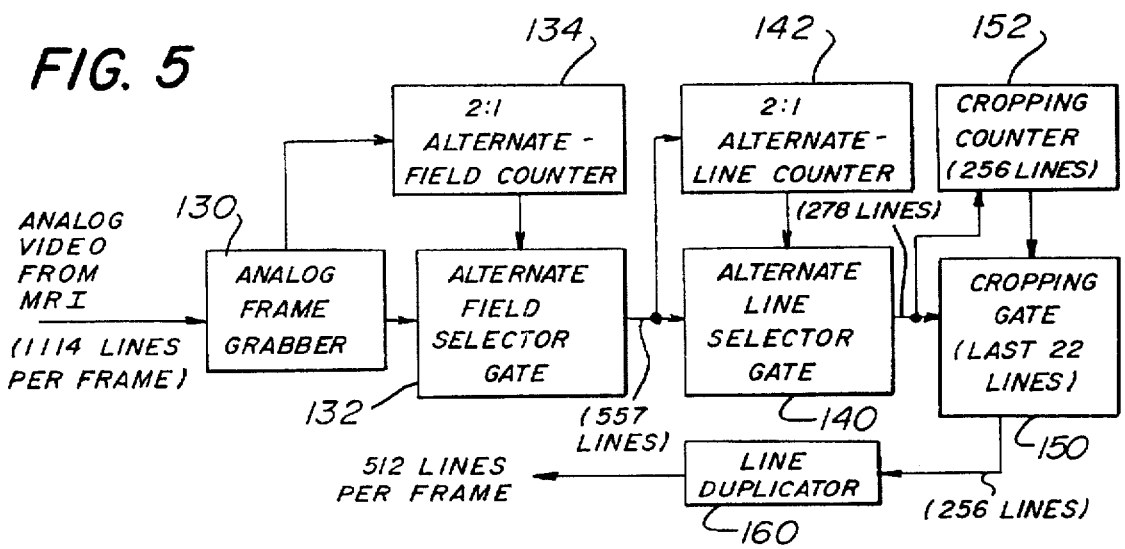
FIG. 5 is a block diagram like that of FIG. 4 but showing an arrangement for converting the video signal from a magnetic resonance imager (MRI) to a different format, preferably NTSC.

Other imaging modalities will typically use other formats, and will require other video converters to convert their analog video signals to the selected standard form. For example, FIG. 5 shows one way of converting the analog video signal of a magnetic resonance (MR) unit from its internal 1114-line raster frame to a standard 525-line NTSC format. An analog frame grabber 130 is again employed, but only alternate raster fields in its output are used. This may be accomplished by an arrangement in which an alternate-field selector gate 132 is turned on for a 60th of a second and off for the next 60th of a second by a 2:1 alternate-field counter 134. The result is that the frame is reduced to one-half of 1114 lines, or 557 lines. The latter signal is then passed through an alternate-line selector gate 140 under the control of a 2:1 alternate-line counter 142. This reduces the raster frame to 278 lines. This signal is passed through a 22-line cropping gate 150, which drops off the last 22 lines of the 278-line frame under the control of cropping counter 152, leaving a 256 frame. The latter signal is passed through a line duplicator 160 which, in effect, repeats each line once before going on to the next line, resulting in a final 512-line frame as desired.

While the functions described with reference to FIGS. 4 and 5 may be embodied in hardware, it is preferred to embody them primarily in firmware on a micro-chip. Similarly, many of the functions of the blocks shown in FIGS. 1 and 2 are preferably performed by programming embodied in firmware or soft-ware, rather than as hardware.

Figure 6:
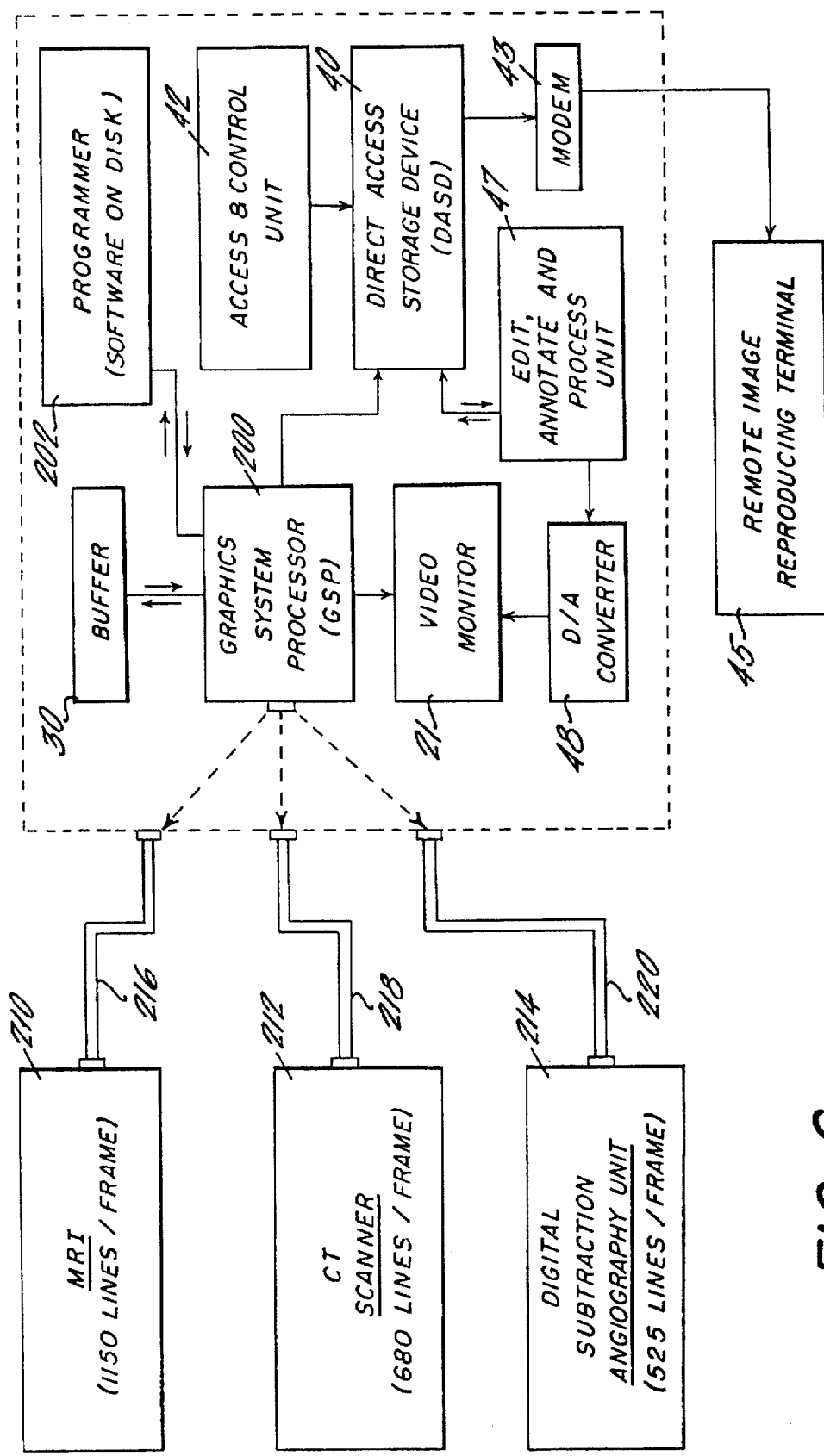
FIG. 6 is a block diagram of another, presently-preferred, embodiment of the invention.
Figure 7:
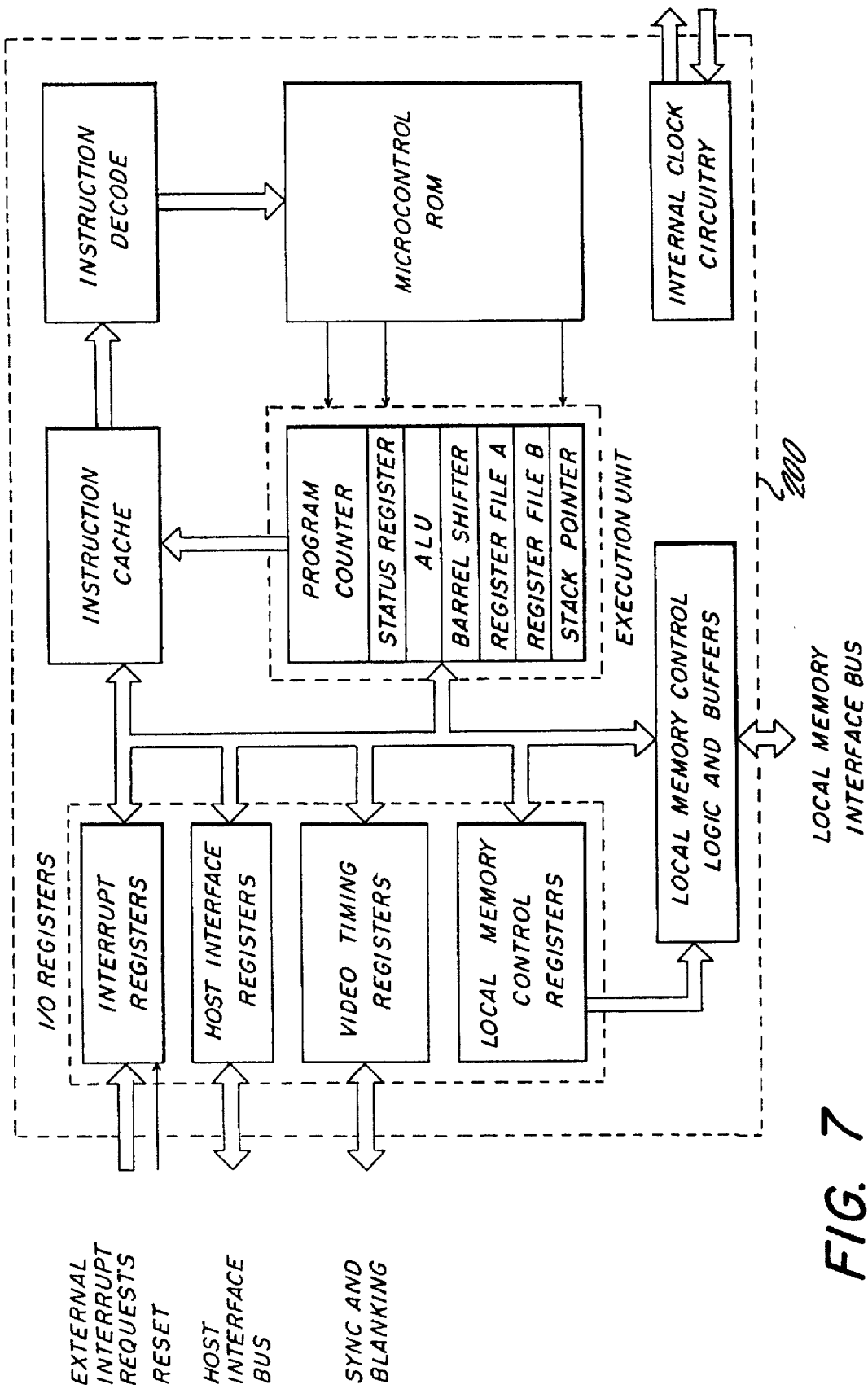
FIG. 7 is a diagram showing the internal architecture of a standard graphics system processor preferred for use in the system of FIG. 6.

Another, presently-preferred embodiment of the invention is shown in FIGS. 6 and 7, in which embodiment the video converter 14, A/D converter 22 and I/O bus interface 38 of FIG. 1 are replaced by a monolithic chip 200 commonly known as a graphics system processor (GSP) and a programmer 202, which together provide the functions of the converter and I/O bus of the earlier-described embodiment and, in addition, render the system operable with any of a variety of different imaging modalities without requiring hardware or firmware changes to accommodate the different formats of the signals from the different modalities. Thus, the system of the invention can be manufactured in a simple form usable with any of a variety of different modalities; furthermore, it can be used at a central station where there is access to a plurality of different types of modalities, and switched between the different modalities as desired, again without requiring hardware or firmware changes. Furthermore, the system is preferably programmed so that, by supplying simple commands to the PC at the central station by way of a standard keyboard, the output signal sent to the remote stations can be in any one of a variety of different formats to accommodate the eventuality that the NTSC format, for example, may not be that most appropriate for the remote station.

Physically, the same type of IBM AT clone as is employed in the earlier described system can again be employed at the central station, but the special board containing the video converter, A/D converter and I/O bus interface is removed and the monolithic GSP chip plugged into an appropriate socket instead.

More particularly, FIG. 6 shows a system which is like that of FIG. 1 except that the graphics system processor (GSP) 200 and the programmer 202 (software on disk) are used in place of the video converter 14, the A/D converter 22 and the I/O bus interface 38 of FIG. 1, and in that, if desired, the graphics system processor may be associated with a signal switching arrangement 203 whereby any selection of the lines from a plurality of different imaging modalities may be connected to the signal input of the GSP 200.

In this example, three such modalities are shown, namely an MRI unit 210 which uses a format of 1,114 horizontal scanning lines per frame, a CT scanner 212 operating at 680 lines per frame, and a digital subtraction angiography unit 214 using 525 lines per frame. As described in connection with the embodiment of FIG. 1, each of these three modalities is provided with a signal output cable, namely cables 216, 218 and 220, respectively, one end of each of which is connected to receive the internal RF analog video image signal of one of the three modalities shown. It is noted that in this example the MRI and CT scanner units produce non-standard analog video, while the DSA unit operates with a NTSC standard 525 lines per frame.

In the operation of the arrangement of FIG. 6, the appropriate one of the single lines 216, 218 and 220 is connected to supply input rf analog video signals to GaP 200, which senses the format of the input signals, converts them to a selected format determined by the programmer 202, and supplies the digitized version of the converted format to the Direct Access Storage Device (DASD) 40 from which the stored image information is read out at appropriate times for transmission through modem 43 to the remote image-reproducing terminal 45. An external buffer 30 is again preferably employed in this example to facilitate the operations of the GSP, although in some cases the buffer may be included in the GSP device itself. The other blocks in FIG. 6 perform substantially the same functions as are described in connection with FIG. 1.

Accordingly, in this embodiment the system responds automatically to standard or non-standard video analog input signals of different formats to convert them to the desired format, digitizes these signals, and outputs the digitized, converted signals in the selected format for storage on disk or other mass storage devices. This approach makes it unnecessary to provide different firmware or hardware systems for use with different imaging modalities, by utilizing software driven firmware in the GSP to synchronize to and to process a variety of analog video inputs from the image modalities. In other words, systems dedicated to use with only one specific imaging modality are not required when the system of FIGS. 6 and 7 is used.

More particularly, the GSP 200 preferably is a Texas Instruments Type TMS34010 graphics systems processor, which includes a "look-up table" storing a list of numbers representing the number of lines per frame in the format of the signals to be received from the various imaging modalities, together with a comparator arrangement such that when any of these modalities supplies analog signal to the GSP, the GSP detects the number of lines per frame in the analog input signal and actuates a conversion procedure appropriate for that number of lines per frame.

The preferred form of GSP includes a multi-synchronous video processor with input look-up tables and a CPU running at 6 MIPS; a graphics processor with DMA access; a video bus capable of handling 36M pixel-per-second transfer; and an array/math coprocessor. This embodiment is arranged to synchronize any input line format having between 0 and 1024 lines per frame, and to convert it to any desired standard or non-standard analog format.

FIG. 7 shows the internal architecture of the preferred type of GSP for this purpose, namely the above-identified Texas Instruments Type TMS34010. The indicated functional external connections are provided by a 16-bit universal bi-directional bus, in known fashion.

It is noted that in this example the DSA modality 214 is assumed to be operating at the NTSC standard of 525 lines per frame, and the system will, if desired, forward the thus-formatted image to the remotely positioned physician's terminals, in this same format; however, as pointed out above, the programmer 202 may change the output of the system to a different format, in the event that the remote terminals are specially adapted to receive some different format.

While the video conversion may be from non-standard format to standard format, in some cases the first format may itself be a standard one but not the desired format; for example, the first format may be 525-line NTSC, while the desired second format may be a different standard using many more lines per frame, as in certain proposed high-definition systems which may come into more general usage in the future. Also, the standard of the second format may not necessarily be NTSC even now, since in other countries a standard format such as PAL (phased alternating line) may be employed. As mentioned above, it is also possible in some applications to transmit the analog video rather than a digitized version thereof; print the analog video directly without transmission it is also possible to digitize the analog video before conversion to the different standard format, rather than vice versa as described above, so long as conversion is effected before transmission to the remote terminal. The system and method may also be applied to the diagnosis or testing of other than living subjects. However, the particular general forms of embodiment shown and described in detail herein have many practical advantages at the present time.

Accordingly, while the invention has been shown and described with particular reference to specific preferred embodiments thereof, it will be understood that it may be embodied in a variety of forms diverse from those specifically shown and described, without departing from the spirit and scope of the invention.

What is claimed is:

1. A system for converting non-standard analog video signals to signals having standard formats for transmission and presentation, the non-standard analog video signals representing images in any of a plurality of first formats, comprising:

converter means responsive to the non-standard analog video signals in the first format for converting the analog video signals to standard analog video signals having a selected different standard analog video format;

digitizing means for digitizing the standard analog video signals to form corresponding digitized image-representing signals;

storage means for storing the digitized image-representing signals;

a remote terminal including a digital-to-analog converter and an image-display device, responsive to the digitized image-representing signals to reproduce the images represented by the non-standard analog video signals;

means for accessing the stored digitized image-representing signals; and means for transmitting the digitized image-representing signals directly to the remote terminal for display on the image-display device.

2. The system of claim 1, further comprising a controllable signal processor connected to the storage means for modifying digitized image-representing signals stored therein, causing a modification of the images reproduced on the remote image-display device.

3. The system of claim 2, wherein the signal processor is controllable to effect selection, annotation and processing of the images reproduced on the remote image-display device.

4. A system for converting a non-standard first analog video signal having one of a plurality of non-standard formats and representing visual images to signals having standard formats for transmission and presentation, the first analog video signals having a first non-standard analog format, comprising:

a transmit side comprising input means for receiving the first analog video signal;

a receive side;

means for converting the first analog video signals to second analog video signals having a different, standard analog format and representing the visual images;

the transmit side further comprising means responsive to the second analog video signals for producing stored digital signals corresponding to the second analog video signals and representing the visual images;

the receive side comprising a remote video display terminal comprising signal receiving means, data processing means, digital-to-analog signal conversion means, and a video monitor; and the transmit side further comprising means for accessing the stored digital signals and for transmitting the digital signals directly to the remote video display terminal for reproduction of the images at the remote video display terminal;

the signal receiving means adapted to receive the digital signals;

the data processing means connected to the signal receiving means and adapted to process the digital signals;

the digital-to-analog signal conversion means connected to the processing means for receiving the digital signals and converting the digital signals to standard analog signals corresponding to the second analog video signals and having a standard analog format different from the non-standard format of the first analog video signals, the standard analog signals representing the visual images; and the video monitor adapted to receive the standard analog signals and to reproduce the visual image represented by the standard analog video signal.

5. A system for conversion of non-standard analog video signals representing images and having a first format to signals having standard formats for transmission and presentation comprising:

video converter means, embodied in a monolithic graphics system processor chip and responsive to the non-standard analog video signals for converting the non-standard analog video signals to corresponding second analog video signals of a second format, representative of the non-standard analog video signals;

analog-to-digital converter means responsive to said second analog video signals to digitize the second analog video signals;

storage means for storing the digitized signals;

access means for accessing the stored digitized signals upon command;

transmission means for transmitting the accessed digitized signals;

remote terminal means for receiving the transmitted digitized signals and for converting the digitized signals to reconstructed analog signals of the second format, representative of the non-standard analog video signals; and display means for receiving the reconstructed analog signals of the second format and for reproducing the images;

the monolithic graphics system processor chip comprising a look-up table means for storing a known number of lines per frame in the first format of the non-standard analog video signals, a comparator means for detecting an actual count of a number of lines per frame and for comparing the actual count to the known number stored in the look-up table, and conversion means to convert the incoming signal to a standard format based on a conversion algorithm appropriate to the non-standard analog video signals detected and any standard format desired;

the video converter means further having a plurality of different modes of operation, each functioning to convert a received format of analog video signals to a selected other format;

the system also comprising format sensing means for receiving non-standard analog video signals having the first format and for producing control signals identifying the format of non-standard analog video signals, and means responsive to the control signals for operating the video converter means in an appropriate mode for the format of the non-standard analog video signals.

6. The system of claim 5, wherein the second format is NTSC format.

7. The system of claim 5, wherein the second format is PAL format.

8. The system of claim 5, wherein the non-standard analog video signals are generated by a medical diagnostic apparatus.

9. The system of claim 8, wherein the medical diagnostic apparatus is a CAT scanning system.

10. The system of claim 8, wherein the medical diagnostic apparatus is an MRI system.

* * * * *